United States Patent [19]

Kyle et al.

[11] Patent Number: 5,543,496

[45] Date of Patent: Aug. 6, 1996

[54] CYCLIC BRADYKININ ANTAGONIST PEPTIDES

[75] Inventors: Donald J. Kyle, Abingdon; Sarvajit Chakravarty, Baltimore, both of Md.

[73] Assignee: Scios Nova Inc., Mountain View, Calif.

[21] Appl. No.: 279,763

[22] Filed: Jul. 25, 1994

Related U.S. Application Data

[63] Continuation of Ser. No. 18,604, Feb. 17, 1993, abandoned.
[51] Int. Cl.$^6$ .............................. C07K 7/18; C07K 7/52; A61K 38/12
[52] U.S. Cl. ........................... 530/314; 530/317; 930/270
[58] Field of Search ..................... 514/9, 11, 2; 530/314, 530/317; 930/270

[56] References Cited

U.S. PATENT DOCUMENTS

| | | | |
|---|---|---|---|
| 4,187,217 | 2/1984 | Chipens et al. | 530/314 |
| 4,242,329 | 12/1980 | Claeson et al. | 424/177 |
| 4,483,850 | 11/1984 | Patchett et al. | 424/177 |
| 4,693,993 | 9/1987 | Stewart et al. | 514/14 |
| 4,801,613 | 1/1989 | Stewart et al. | 514/14 |
| 4,822,894 | 4/1989 | Geiger et al. | 548/252 |
| 4,923,963 | 5/1990 | Stewart et al. | 530/314 |

FOREIGN PATENT DOCUMENTS

| | | |
|---|---|---|
| 0330241 | 8/1989 | European Pat. Off. . |
| 0370453 | 5/1990 | European Pat. Off. . |
| 0413277 | 2/1991 | European Pat. Off. . |
| 0472220 | 2/1992 | European Pat. Off. . |
| 0892871 | 9/1983 | U.S.S.R. . |
| 92/18156 | 10/1992 | WIPO . |
| 92/18155 | 10/1992 | WIPO . |

OTHER PUBLICATIONS

Karanewsky et al., "(Phosphinyloxy)acyl amino acids inhibitors of angiotensin converting enzyme. 2. Terminal amino acid analogues of (S)–1–[6–amino–2[[hydroxy(4–phenylbutyl)phosphinyl]oxy]–1–oxohexyl]–L–proline" *J. Med. Chem.* (1990) 33(5):1459–1469.

Smith et al., "Synthesis and pharmacological activity of angiotensin converting enzyme inhibitors: N–(mercaptoacyl)–4–substituted–(S)–prolines" *J. Med. Chem.* (1988) 31(4):875–885.

Krapcho et al., "Angiotensin converting enzyme inhibitors. Mercaptan, carboxyalkyl dipeptide, and phosphinic acid inhibitors incorporating 4–substituted prolines" *J. Med. Chem.* (1988) 31(6):1148–1160.

Hock et al., "Hoe 140 a new potent and long acting bradykinin antagonist: *in vitro* studies" *Br. J. Pharmacol. (1991) 102:769–744.

Wirth et al., "Hoe 140 a new potent and long acting bradykinin antagonist: *in vivo* studies" *Br. J. Pharmacol.* (1991) 102:774–777.

Pongracic et al., "A competitive kinin receptor antagonist, [DArg$^0$, Hyp$^3$, DPhe$^7$]–bradykinin, does not affect the response to nasal provocation with bradykinin" *Br. J. Pharmacol.* (1991) 31:287–294.

Higgins et al., "A study of the efficacy of the bradykinin antagonist NPC567 in rhinovirus infections in human volunteers" *Chemical Abstracts* (1991) 114:220805d.

Soler et al., "A bradykinin antagonist modifies antigen–induced airway hyper–responsiveness and airway inflammation in allergic sheep" *Am. Rev. Respir. Dis.* (1989) A327.

Stewart, John M., "Hydroxyproline analogs of bradykinin" *J. Med. Chem.* (1974) 17(5)537–539.

Stewart, John M., "Chemistry and biologic activity of peptides related to bradykinin" *Handbook of Experimental Pharmacol.* (1979) vol. XXV Supp, Springer–Verlag Berlin Heidelberg NY.

Barabe et al. "New agonist and antagonist analogues of bradykinin" *Can. J. Physiol. Pharmacol.* (1984) 62:627–629.

Vavrek et al., "Smooth muscle selectivity in bradykinin analogs with multiple D–amino acid substitutions", Dept. of Biochem., University of Colorado School of Medicine, Denver, Colorado.

Rifo et al., "Bradykinin receptor antagonists used to characterize the heterogeneity of bradykinin–induced responses in rat vas deferens" *Eur. J. Pharmacol.* (1987) 142:305–312.

Zeitlin et al., "Mobilization of tissue kallikrein in inflammatory disease of the colon" Wolfson Labs, Gastrointestinal Unit, West General Hospital and Dept. of Clinical Surgery, Univ. of Edinburgh (1972) pp. 113–138.

Suzuki et al., "Synthesis of every kind of peptide fragments of bradykinin" *Chem. Pharm. Bull.* (1969) 17:1671–1678.

Nikifomovich et al., *Proc. Eur. Pept. Symp, 17th* (1983) 735–739.

Stewart et al., *Adv. Exp. Med. Biol.* (Kinins, Pt. A) (1983) 585–589.

Chipens et al., *Pept. Struct. Biol. Funct., 6th Proc. Am. Pept. Symp.* (1979) 567–570.

Fox et al., "Raman studies on bradykinin and a cyclic bradykinin analog" *7th Proc. Natl. Am. Peptide Symp.* (1981) 323–326.

(List continued on next page.)

*Primary Examiner*—Margaret Parr
*Assistant Examiner*—T. D. Wessendorf
*Attorney, Agent, or Firm*—Peter R. Shearer

[57] ABSTRACT

Cyclic compounds based on a modified bradykinin sequence are potent bradykinin receptor antagonists. Amino acid substitutions are made at postions 2 and 5 or 6 to facilitate the cyclization of the peptide through covalent bonding of the amino acid side chains.

The analogs produced are useful in treating conditions and diseases of a mammal and human in which an excess of bradykinin or related kinins are produced or injected such as by insect bites.

1 Claim, No Drawings

OTHER PUBLICATIONS

Kyle et al., "Design and conformational analysis of serveral hightly potent bradykinin receptor antagonists" *J. Med. Chem.* (1991) 34(3):1230–1233.

Manning, Maurice, "Approach to the design of selective *in vivo* antagonists of biologically active peptides based on conformational restriction via gem–dialkyl substitutions and S—S bridging" *Proc. Intl. Symp. Substance P.* (1983) 14–15.

Stewart et al., "Bradykinin chemistry: agonists and antagonists" *International Conference Kinin 81 Munich.*

Chipens et al., "Cyclic analogues of bradykinin" *Int. J. Peptide Protein Res.* (1985) 26:460–468.

Chakravarty et al. "Design of potent, cyclic peptide bradykinin receptor antagonists from conformationally constrained linear peptides" *J. Med. Chem. (1993) 36:2569–2571.*

CYCLIC BRADYKININ ANTAGONIST PEPTIDES

This application is a continuation of application Ser. No. 08/018,604 filed Feb. 17, 1993, now abandoned.

FIELD OF THE INVENTION

This invention relates to compounds which are bradykinin receptor antagonists, pharmaceutical compositions and methods for using these compounds to antagonize the effects of bradykinin in mammals, including humans. More particularly, the invention relates to cyclic peptides which are potent bradykinin receptor antagonists.

DESCRIPTION OF THE PRIOR ART

Bradykinin (BK) is a nonapeptide generated as a result of the activity of kallikreins, a group of proteolytic enzymes present in most tissues and body fluids, on kininogens. Once released, kinins produce many physiological responses, including pain and hyperalgesia by stimulating C- and A-fibers in the periphery. There is also considerable evidence that kinins contribute to the inflammatory response.

Bradykinin, and its physiologically important related peptides kallidin (Lys-bradykinin) and Met-Lys-bradykinin, exhibit physiological actions which qualify them as mediators of inflammatory reactions, hypotensive states, and pain. Bradykinin is overproduced in pathological conditions such as septic shock, anaphylaxis, rhinitis, asthma, inflammatory bowel disease, and certain other conditions including acute pancreatitis, post-gastrectomy dumping syndrome, carcinoid syndrome, migraine, and angioneurotic edema. The production of bradykinin from the plasma results in pain at the site of the pathological condition, and the overproduction intensifies the pain directly or via bradykinin-induced activation of the arachidonic acid pathway which produces prostaglandins and leukotrienes, the more distal and actual mediators of inflammation.

In addition to its proinflammatory effects, bradykinin is a vasodilator. Because of its ability to lower blood pressure, bradykinin has been implicated in the pathogenesis of several shock syndromes, particularly septic or endotoxic shock. Bradykinin is also a potent in animals and asthmatic subjects and it has been implicated as a contributor to the pathogenesis of airway inflammatory conditions such as allergic asthma and rhinitis.

Thus, a bradykinin receptor antagonist is expected to possess a number of desirable biological effects in the treatment, for example, of inflammation, septic shock, asthma, burn pain, rhinitis, and allergy.

The search for understanding the mechanism of action of bradykinin, which is essential for the development of useful tools for diagnostic use, and for the development of therapeutic agents aimed at alleviating the intense pain caused by the production and overproduction of bradykinin, has been hindered by the lack of specific sequence-related competitive antagonists of bradykinin.

Several non-peptide, non-specific and non-selective antagonists of one or more of the biological activities of bradykinin have been described among compounds as diverse as analgesics and anti-inflammatory substances, which act via the prostaglandin system and not directly on bradykinin receptors. These are antihistamines, bradykinin-antibodies, benzodiazepine derivatives, high molecular weight ethylene oxide polymers, gallic acid esters, and serotonin inhibitors. None of these compounds or classes of compounds specifically inhibit the effects of bradykinin.

Heptyl esters of various amino acid-containing substances, such as single basic amino acids the dipeptide Phe-Gly, and analogs of C-terminal peptide fragments of bradykinin (i.e., Pro-Phe-Arg) have been reported as anti-bradykinin substances. When tested in bradykinin assay systems, they prove to be weak partial agonists/antagonists, depending on the dose, with little specificity for inhibiting bradykinin action.

Preparations of damaged vascular tissue have been reported to respond to bradykinin analogs which lack the C-terminal arginine residue, but not to bradykinin itself, and analogs of these des-Arg(9)-bradykinins have been developed as antagonists for the B1-mediated activities of bradykinin. Furthermore, several bradykinin analogs containing the O-methyl ether of Tyr residues at positions 5 and/or 8 have been reported to produce mixed agonist/antagonist activity on isolated uteri of galactosemic rats, but not on normal rats.

Other changes in the bradykinin molecule have been additions of amino acids at the N-terminal end which affect the rate of enzymatic degradation of bradykinin in vivo.

It has been reported that the half life of bradykinin in the systemic circulation is less than 30 seconds. Bradykinin appears to be completely destroyed (98–99% destruction) on a single passage through the pulmonary circulation as determined in an anesthetized rat by measuring the depressor effects of an agonist following intra-aortic (i.a.) (bypassing the pulmonary circulation) and intravenous (i.v.) administration. Resistance of bradykinin agonists to pulmonary kininase destruction in vivo also appears promoted by addition of single (i.e., D-Arg-, D-Lys-, Lys-) and double (D-Lys-Lys-) basic amino acid residues to the N-terminus of the bradykinin sequence. The addition of the dipeptide Lys-Lys to the N-terminus of bradykinin agonists has been reported to confer complete resistance to in vivo destruction on initial passage through the pulmonary circulation.

Several research groups have prepared bradykinin receptor antagonists. Stewart and Vavrek in U.S. Pat. No. 4,801,613, (which reference is incorporated in its entirety herein) disclose a series of bradykinin antagonists wherein the L-Pro at the 7-position of the peptide hormone bradykinin or other substituted analogs of bradykinin is substituted with an aromatic amino acid of the D-configuration which converts bradykinin agonists into bradykinin antagonists. The specific L-Pro substitutions are selected from the group consisting of D-Nal, D-PNF, D-Phe, D-Tyr, D-Pal, D-OMT, D-Thi, D-Ala, D-Trp, D-His, D-Homo-Phe, D-Phe, pCl-D-Phe (CDF), D-Phg, D-Val, D-Ile, D-Leu, and MDY.

In U.S. Pat. No. 4,693,993, also to Stewart and Vavrek, additional L-Pro substitution materials are disclosed.

Published PCT application WO 92/18156 discloses and claims additional L-Pro substitution materials with hydroxyproline ether and thioether compounds. WO 92/18155 additionally discloses substitutions of the L-Phe at position 8 with hydroxy proline ethers and thioethers.

U.S. Pat. No. 4,242,329 to Claeson et al. disclose the formation of bradykinin-inhibiting tripeptide derivatives. A process for producing said tripeptide derivatives by synthesis and purification methods which are known in the peptide chemistry is also disclosed as well as pharmaceutical preparations comprising the tripeptide derivative.

Published European Patent Applications No. 0 413 277 A1 and 0 370 453 AZ disclose bradykinin antagonists.

Chipens et al. (Int. J. Peptide Protein Res., 1985, 26:460–468) discloses cyclic bradykinin molecules which have agonist activity.

Fox et al. (7th Proceeding of National American Peptide Symposium, p.323) disclose a bradykinin analog wherein the amino acids positions at 1 and 6 are replaced with cysteines and cyclized. This analog exhibited bradykinin-like biological activity in various bradykinin assays.

SUMMARY OF THE INVENTION

The present invention resides in the discovery that the novel cyclic compounds identified below, are potent bradykinin receptor antagonists. The compounds are useful in the treatment of various diseases including inflammatory disorders, asthma, septic shock, and burn pain. Included in the invention are pharmaceutical compositions containing the inventive compounds and methods of using the compounds as bradykinin receptor antagonists.

More particularly, the invention relates to a modification of the sequence of the mammalian peptide hormone bradykinin and pharmaceutically acceptable salts thereof.

The bradykinin modification contemplated by this invention includes cyclization of the bradykinin molecule to provide a rigid structure having enhanced affinity for the bradykinin receptor. Specifically, the Pro residue at position 2 and the Phe residue at position 5 or the Ser residue at position 6 are replaced with amino acid residues which form a covalent bond through their side chains to cyclize the structure. Examples of suitable amino acid substitutions include, but are not limited to, Cys for disulfide bond formation or a combination of Lys and Glu or Asp for amide bond formation.

Native Bradykinin has the amino acid structure shown in Table I:

TABLE I

| N — | A — | B — | C — | D — | E — | F — | G — | H — | I — | J — | Cn |
|---|---|---|---|---|---|---|---|---|---|---|---|
| | Arg— | Pro— | Pro— | Gly— | Phe— | Ser— | Pro— | Phe— | Arg | | |
| | 1 | 2 | 3 | 4 | 5 | 6 | 7 | 8 | 9 | | |

The invention relates more specifically to the formation of peptides having the formula:

N—A—B—X—H—I—J—Cn wherein N is hydrogen;

A and B are independently selected from the group consisting of L-Arg, D-Arg, D-Gln, L-Gln, D-Asn, L-Asn, N-ε-acetyl-D-lysine, ε-acetyl-L-lysine, NG-p-tosyl-Arg, NG-nitro-Arg, Lys-Lys, acetyl-D-Arg, L-Citrulline, L-Lys, Sar, and D-Lys;

X is selected from the group consisting of the following formulas:

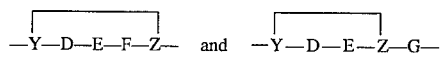

wherein Y and Z form a covalent bond through the amino acid side chains;

D and E are independently selected from the group consisting of Pro, 4Hyp, Tic, Ala, Gly, Oic, dehydro-Pro, Aoc, L-azetidine-2-carboxylic acid, Thz and Aib;

F is selected from the group consisting of Phe, Thi, Trp, Tyr, Leu, Ile, Tic, Oic, homoPhe, phenylGly, β-cyclohexylalanine, Nal, and Val;

G is a direct bond or is selected from the group consisting of Ser, Thr, Gly, Val, Ala, Cys and Tyr;

H is selected form the group consisting of D-Phe, D-Tic, D-Pro, and a compound of the D-configuration having the formula:

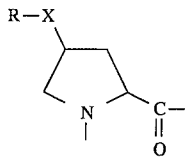

wherein R is selected from the group consisting of H, $C_1$–$C_6$ alkyl, substituted $C_1$–$C_6$ alkyl, $C_2$–$C_8$ alkenyl, $C_3$–$C_8$ cycloalkyl, $C_3$–$C_8$ cycloalkyl substituted $C_1$–$C_6$ alkyl, an aryl group, a substituted aryl group, an arylalkyl group, and a group of the formula $R^1NHC(O)$— where $R^1$ is $C_1$–$C_6$ alkyl or aryl, and where X is either $SO_n$ or oxygen, and n=0, 1, or 2;

I is selected from the group consisting of Oic, Aoc, Thz, Tic, L-indoline-2-carboxylic acid, octahydro-1H-isoindole-1-carboxylic acid, pipecolinic acid, Pro, 4Hyp, azetidine-2-carboxylic acid, Aib, Leu, Ile, Val, Thi, Phe, homoPhe, and compounds of the following formula:

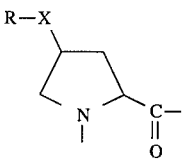

wherein R is selected from the group consisting of H, $C_1$–$C_6$ alkyl, substituted $C_1$–$C_6$ alkyl, $C_2$–$C_8$ alkenyl, $C_3$–$C_8$ cycloalkyl, $C_3$–$C_8$ cycloalkyl substituted $C_1$–$C_6$ alkyl, an aryl group, a substituted aryl group, an arylalkyl group, and a group of the formula $R^1NHC(O)$— where $R^1$ is $C_1$–$C_6$ alkyl or aryl, and where X is either $SO_n$ or oxygen, and n=0, 1, or 2;

J is selected from the group consisting of Arg, Orn, Asn, Gln, and Lys;

CN is a hydroxyl group or a C-terminal extension is selected from the group consisting of amide, alkoxy group, an acidic, basic or neutral aliphatic, aromatic, and cyclic amino acid residue of the D- or L-configuation, and a peptide extension composed of D- or L-amino acids; and pharmaceutically accepable salts thereof.

Another embodiment of the invention involves a pharmaceutical composition useful as a bradykinin receptor antagonist comprising a pharmaceutical carrier and an effective amount of the novel bradykinin-type peptide. The invention also involves a process for antagonizing bradykinin receptor activity in mammals which comprises administering to a subject an effective amount of the novel compound to antagonize bradykinin receptor activity.

A further embodiment involves a pharmaceutical preparation for treating local pain and inflammation from burns, wounds, cuts, rashes and other such trauma, and pathological conditions caused by the production of bradykinin or related kinins by an animal which comprises administering an effective amount of the novel peptide sufficient to antagonize bradykinin with a suitable pharmaceutical carrier. Another aspect of this invention involves a process for treating local pain and inflammation which comprises administering an effective amount of the pharmaceutical preparation to an animal in need thereof.

DETAILED DESCRIPTION OF THE INVENTION

The present cyclic compounds which are bradykinin receptor antagonists have the following formula:

Formula 1

N—A—B—X—H—I—J—Cn wherein N is hydrogen;

A and B are independently selected from the group consisting of L-Arg, D-Arg, D-Gln, L-Gln, D-Asn, L-Asn, N-ε-acetyl-D-lysine, ε-acetyl-L-lysine, $N^G$-p-tosyl-Arg, $N^G$-nitro-Arg, Lys-Lys, acetyl-D-Arg, L-Citrulline, L-Lys, Sar, and D-Lys;

X is selected from the group consisting of the following formulas:

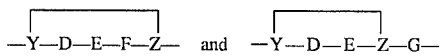

—Y—D—E—F—Z—  and  —Y—D—E—Z—G— wherein Y and Z are amino acids which form a covalent bond through the amino acid side chains;

D and E are independently selected from the group consisting of Pro, 4Hyp, Tic, Ala, Gly, Oic, dehydro-Pro, Aoc, L-azetidine- 2-carboxylic acid, Thz and Aib;

F is selected from the group consisting of Phe, Thi, Trp, Tyr, Leu, Ile, Tic, Oic, homoPhe, phenylGly, β-cyclohexylalanine Nal, and Val;

G is a direct bond or is selected from the group consisting of Ser, Thr, 4Hyp, Gly, Ala, Val, Cys, and Tyr;

H is selected from the group consisting of D-Phe, D-Tic, D-Pro, and a compound of D-configuration having the formula:

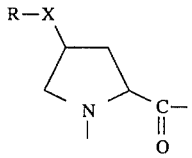

wherein R is selected from the group consisting of H, $C_1-C_6$ alkyl, $C_2-C_8$ alkenyl, $C_3-C_8$ cycloalkyl, $C_3-C_8$ cycloalkyl substituted $C_1-C_6$ alkyl, an aryl group, a substituted aryl group, an arylalkyl group, and a group of the formula $R^1NHC(O)$—where $R^1$ is $C_1-C_6$ alkyl or aryl, and where X is either $SO_n$ or oxygen, and n=0, 1, or 2;

I is selected from the group consisting of Oic, Aoc, Thz, Tic, L-infoline- 2-carboxylic acid, octahydro-1H-isoindole-1-carboxylic acid, pipecolinic acid, Pro, 4Hyp, azetidine-2-carboxylic acid, Aib, Leu, Ile, Val, Thi, Phe, homoPhe, and compounds of the following formula:

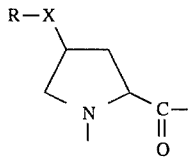

Wherein R is selected from the group consisting of H, $C_1-C_6$ alkyl, substituted $C_1-C_6$ alkyl, $C_2-C_8$ alkenyl, $C_3-C_8$ cycloalkyl, $C_3-C_8$ cycloalkyl substituted $C_1-C_6$ alkyl, an aryl group, a substituted aryl group, an arylalkyl group, and a group of the formula $R^1NHC(O)$—where $R^1$ is $C_1-C_6$ alkyl or aryl, and where X is either $SO_n$ or oxygen, and n=0, 1, or 2;

J is selected from the group consisting of Arg, Orn, Asn, Gln, and Lys;

Cn is a hydroxyl group or a C-terminal extension selected from the group consisting of amide, alkoxy group, an acidic, basic or neutral aliphatic, aromatic, and cyclic amino acid residue of the D- or L-configuration, and a peptide extension composed of D- or L-amino acids; and pharmaceutically accepable salts thereof.

The designation

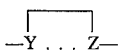

—Y ... Z— is defined herein such that Y and Z are amino acid residues in the bradykinin receptor antagonist molecule which form a covalent bond through their side chains (as indicated by

).

The solid lines indicate conventional peptide bonds. For preferred peptides, Y and Z are selected such that both are Cys, one is Glu and the other is Lys, or one is Asp and the other is Lys.

Formula 2

Particularly preferred is a peptide wherein:

A is D-Arg;

B is Arg;

X and Y are selected such that both are Cys, or one is Lys and the other is either Asp or Glu;

D and E are independently selected from the group consisting of Pro, 4Hyp, Oic, Tic, Ala and Gly;

F is selected from the group consisting of Phe, Thi, Trp, and Tyr;

G is a direct bond or Ser;

H is selected form the group consisting of D-Phe, D-Tic, D-Hype (trans propyl) D-Hype (trans thiophenyl) and D-Hype (trans phenyl propyl);

I is selected from the group consisting of Phe, Oic, Aoc, Hype (propyl), Hype (thio phenyl) and Hype (phenyl propyl);

J is Arg; and

Cn is a hydroxyl group.

Formula 3

Most preferred is a peptide wherein:

Y and Z are both Cys;

D is selected from the group consisting of Pro, Gly, and 4Hyp;

E is selected from the group consisting of Gly and Ala; and

F is selected from the group consisting of Phe and Thi.

Other preferred cyclic peptides of the invention include, but are not limited to the following compounds, wherein signifies a covalent attachment between the side chains of the amino acids:

H—D—Arg—Arg—Cys—Pro—Gly—Phe—Cys—D—Tic—Oic—Arg—OH
H—D—Arg—Arg—Asp—Pro—Gly—Phe—Lys—D—Tic—Oic—Arg—OH
H—D—Arg—Arg—Glu—Pro—Gly—Phe—Lys—D—Tic—Oic—Arg—OH
H—D—Arg—Arg—Lys—Pro—Gly—Phe—Asp—D—Tic—Oic—Arg—OH
H—D—Arg—Arg—Lys—Pro—Gly—Phe—Glu—D—Tic—Oic—Arg—OH
H—D—Arg—Arg—Cys—Gly—Gly—Phe—Cys—D—Tic—Oic—Arg—OH
H—D—Arg—Arg—Asp—Gly—Gly—Phe—Lys—D—Tic—Oic—Arg—OH
H—D—Arg—Arg—Glu—Gly—Gly—Phe—Lys—D—Tic—Oic—Arg—OH
H—D—Arg—Arg—Lys—Gly—Gly—Phe—Asp—D—Tic—Oic—Arg—OH
H—D—Arg—Arg—Lys—Gly—Gly—Phe—Glu—D—Tic—Oic—Arg—OH
H—D—Arg—Arg—Cys—Pro—Gly—Phe—Cys—D-Hype(trans thiophenyl)—Oic—Arg—OH
H—D—Arg—Arg—Asp—Pro—Gly—Phe—Lys—D-Hype(trans thiophenyl)—Oic—Arg—OH
H—D—Arg—Arg—Glu—Pro—Gly—Phe—Lys—D-Hype(trans thiophenyl)—Oic—Arg—OH
H—D—Arg—Arg—Lys—Pro—Gly—Phe—Asp—D-Hype(trans thiophenyl)—Oic—Arg—OH
H—D—Arg—Arg—Lys—Pro—Gly—Phe—Glu—D-Hype(trans thiophenyl)—Oic—Arg—OH
H—D—Arg—Arg—Cys—Gly—Gly—Phe—Cys—D-Hype(trans thiophenyl)—Oic—Arg—OH
H—D—Arg—Arg—Asp—Gly—Gly—Phe—Lys—D-Hype(trans thiophenyl)—Oic—Arg—OH
H—D—Arg—Arg—Glu—Gly—Gly—Phe—Lys—D-Hype(trans thiophenyl)—Oic—Arg—OH
H—D—Arg—Arg—Lys—Gly—Gly—Phe—Asp—D-Hype(trans thiophenyl)—Oic—Arg—OH
H—D—Arg—Arg—Lys—Gly—Gly—Phe—Glu—D-Hype(trans thiophenyl)—Oic—Arg—OH
H—D—Arg—Arg—Cys—Pro—Gly—Cys—Ser—D—Tic—Oic—Arg—OH
H—D—Arg—Arg—Asp—Pro—Gly—Lys—Ser—D—Tic—Oic—Arg—OH
H—D—Arg—Arg—Glu—Pro—Gly—Lys—Ser—D—Tic—Oic—Arg—OH
H—D—Arg—Arg—Lys—Pro—Gly—Asp—Ser—D—Tic—Oic—Arg—OH
H—D—Arg—Arg—Lys—Pro—Gly—Glu—Ser—D—Tic—Oic—Arg—OH -continued H—D—Arg—Arg—Cys—Gly—Gly—Cys—Ser—D—Tic—Oic—Arg—OH H—D—Arg—Arg—Asp—Gly—Gly—Lys—Ser—D—Tic—Oic—Arg—OH H—D—Arg—Arg—Glu—Gly—Gly—Lys—Ser—D—Tic—Oic—Arg—OH H—D—Arg—Arg—Lys—Gly—Gly—Asp—Ser—D—Tic—Oic—Arg—OH H—D—Arg—Arg—Lys—Gly—Gly—Glu—Ser—D—Tic—Oic—Arg—OH H—D—Arg—Arg—Cys—Pro—Gly—Cys—Ser—D-Hype(trans thiophenyl)—Oic—Arg—OH H—D—Arg—Arg—Asp—Pro—Gly—Lys—Ser—D-Hype(trans thiophenyl)—Oic—Arg—OH H—D—Arg—Arg—Glu—Pro—Gly—Lys—Ser—D-Hype(trans thiophenyl)—Oic—Arg—OH H—D—Arg—Arg—Lys—Pro—Gly—Asp—Ser—D-Hype(trans thiophenyl)—Oic—Arg—OH H—D—Arg—Arg—Lys—Pro—Gly—Glu—Ser—D-Hype(trans thiophenyl)—Oic—Arg—OH H—D—Arg—Arg—Cys—Gly—Gly—Cys—Ser—D-Hype(trans thiophenyl)—Oic—Arg—OH H—D—Arg—Arg—Asp—Gly—Gly—Lys—Ser—D-Hype(trans thiophenyl)—Oic—Arg—OH H—D—Arg—Arg—Glu—Gly—Gly—Lys—Ser—D-Hype(trans thiophenyl)—Oic—Arg—OH H—D—Arg—Arg—Lys—Gly—Gly—Asp—Ser—D-Hype(trans thiophenyl)—Oic—Arg—OH H—D—Arg—Arg—Lys—Gly—Gly—Glu—Ser—D-Hype(trans thiophenyl)—Oic—Arg—OH As used in the specification and claims, "alkyl" is a paraffinic hydrocarbon group which may be derived from an alkane by dropping one hydrogen from the formula, such as methyl, ethyl, propyl, isopropyl, butyl, and so forth; "substituted $C_1$–$C_6$ alkyl" is a branched alkyl, such as methyl butyl; "aryl" is an aromatic ring compound such as benzene, phenyl, napthyl; "substituted aryl" is a substituted aromatic ring, such as nitro substitution, or halogen substitution; and "aralkyl" is a aryl being attached through an alkyl chain, straignt or branched, containing from one through six carbons, such as a phenylpropyl group. A "direct bond" is a bond which replaces a particular amino acid compound between adjacent amino acids and which amino acid may also be indicated to be absent by the term "null". The phrase "a suitable amine protecting group" is a group, such as BOC (t-butyloxy-carbonyl-) protecting group which protects the amine moiety from reaction and which can be removed under mild conditions so as not to affect the rest of the molecule.

Definitions of the amino acid abbreviations used herein are as follows:

Arg is arginine; Ala is alanine; Aib is 2-aminoisobytyric acid; Aoc is (S,S,S)-2-azabicyclo[3.3.0]octane-3-carboxylic acid; Asn is asparagine; Asp is aspartic acid; Cys is cysteine; Eac is ε-aminocaproic acid; Gln is glutamine; Glu is glutamic acid; Gly is glycine; Ile is isoleucine; Leu is leucine; Lys is lysine; Met is methionine; Nal is beta-2-naphthylalanine; Orn is ornithine; Pro is proline; dehydroPro is 3,4-dehydroproline, homoPhe is homophenylalanine; 4Hyp is 4-hydroxyproline; Ser is serine; Sar is sarcosine; Thi is beta-2-thienylalanine; Thr is threonine; Thz is thiazolidine-4-carboxylic acid; Phe is phenylalanine; phenylGly is 2-phenylglycine; Tic is tetrahydroisoquinoline-3-carboxylic acid; Oic is (2S, 3aS, 7aS)-octahydro-1H-indole-2-carboxylic acid; Val is valine; prenyl is a 3-methyl-2-butenyl radical. D-Hype (trans propyl) is 4S-D-prolyl propyl ether and represents

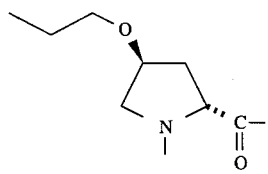

D-Hype (trans thiophenyl) is 4S-D-prolyl phenyl thioether, also known as D-4-hydroxyproline trans phenylthioether also known as D-Hyp S(trans phenyl) and represents

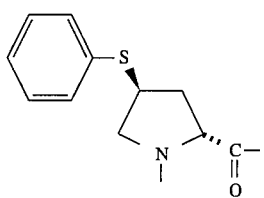

D-Hype (trans-phenyl propyl) represents

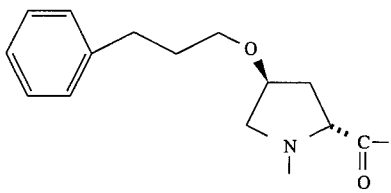

D-Hype (trans-2-methyl butyl) represents

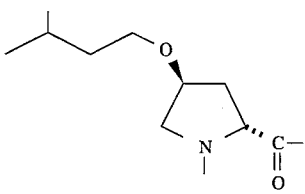

D-Hype (trans-ethyl) represents

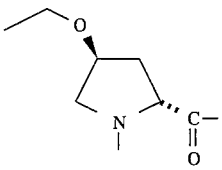

D-Hype (trans-methyl) represents

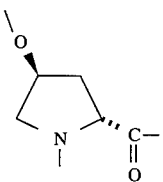

Aoc can be prepared by the method of V. Teetz, R. Geiger and H. Gaul, *Tetrahedron Lett.* (1984), 4479. Tic can be prepared by the method of K. Hayashi, Y. Ozaki, K. Nunami and N. Yoneda, *Chem. Pharm. Bull.* (1983) 31, 312.

All amino acids residues, except Gly, and Sar described in the specification are preferably of the L-configuration unless otherwise specified. It would be recognized, however, that the 7 position must always be the D-configuration whereas the hydroxyproline ethers and thioethers of position 8 may be either in the D- or L- configuration. The hydroxyproline ethers at position 7 are preferably in a trans configuration, whereas the hydroxyproline ethers at position can be in either the cis or trans configuration. The symbols and abbreviations used for amino acids, their derivatives and protecting groups, and peptides and their salts are those customarily used in peptide chemistry. (See *Biochem. J.* (1972), 126, 773).

The side chain of the amino acid at the Y position (position 2) forms a covalent bond with the side chain of the amino acid at the Z position (either at position 5 or at position 6.) The amino acids at postion Y and Z can be any amino acid that will form a suitable covalent bond through the side chains. Preferred amino acids include cysteine at both positions or a combination of Lys and Glu or Asp. Most preferred is Cys at both Y and Z positions which forms a disulfide bond. An amide bond is formed when the combination of Lys and Glu or Asp is utilized.

The synthesis of the peptides of this invention including derivation, activation, and coupling of protected amino acid residues, and their purification, and the analytical methods for determing identity and purity are included in the general body of knowledge of peptide chemistry, as described in Houben Weyl *Methoden der Organischen Chemie*, (1974), Vol. 16, parts I & II for solution-phase synthesis, and in *Solid Phase Peptide Synthesis,* (1984), by Stewart and Young for synthesis by the solid-phase method of Merrifield.

Any chemist skilled in the art of peptide synthesis can synthesize the peptides of this invention by standard solution methods or by manual or automated solid phase methods.

The appropriate hydroxyproline substituents used at position 7 or 8 are prepared by the process described in PCT publications WO 92/18155 and WO 92/18156 which are herein incorporated by reference and depicted in the schemes shown below. The starting materials are commercially available and can be prepared by known procedures. Both the cis and trans stereoisomers can be prepared by these means and are within the scope of the present invention. In Scheme II, M represents sodium, potassium and other useable salts such as alkaline earth metals and alkali metals and X is oxygen or sulfur.

Scheme I

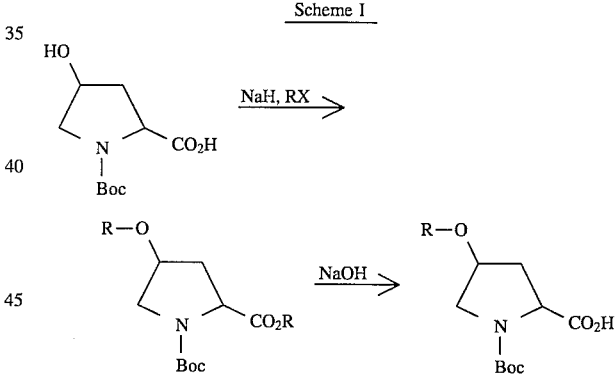

Alternately, they also can be prepared by the method of Scheme II from commercially available starting materials.

Scheme II

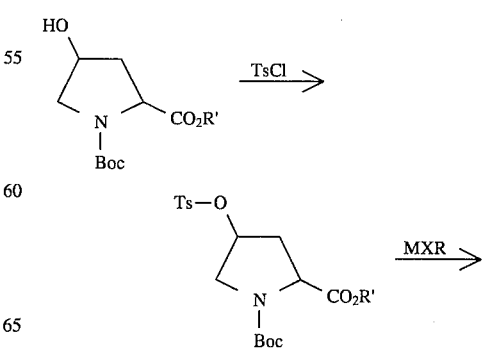

-continued
Scheme II

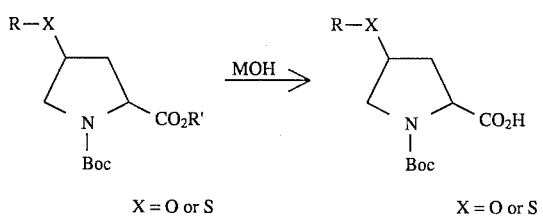

X = O or S          X = O or S

The preparation of compounds for administration in pharmaceutical preparations may be performed in a variety of methods well known to those skilled in the art. Appropriate pharmaceutically acceptable salts within the scope of he invention are those derived from mineral acids such as hydrochloric acid, hydrobromic acid, phosphoric acid, nitric acid, and sulfuric acid; and organic acids such as tartaric acid, fumaric acid, lactic acid, oxalic acid, ethylsulfonic acid, p-toluenesulfonic acid, and the like, giving the hydrochloride, sulfate, phosphate, nitrate, methanesulfonate, tartrate, benzenesulfonate, p-toluensulfonate, and the like, salt, respectively.

The compounds of the invention may contain an asymmetric carbon atom. Thus, the invention includes the individual stereoisomers, and the mixtures thereof. The individual isomers may be prepared or isolated by methods known in the art.

ADMINISTRATION AND USE

Therapeutic applications of the novel bradykinin antagonists include not only treatment for the production of bradykinin or related kinins by the animal but also the injection of bradykinin related peptides into an animal as a result of bites and stings. Topical application alone or in combination with subcutaneous utilization of the bradykinin antagonists of the invention can be employed to treat the effects of bradykinin-related peptides causing pain, inflammation and swelling.

The therapeutic use of bradykinin antagonists of this invention for other traumatic inflammatory or pathological conditions which are known to be mediated by bradykinin or exacerbated by an overproduction of bradykinin can also be achieved. These conditions include local trauma such as wounds, burns, rashes, angina, arthritis, asthma, allergies, rhinitis, shock, inflammatory bowel disease, low blood pressure, and systemic treatment of pain and inflammation.

In parenteral administration of the novel compounds and compositions of the invention the compounds may be formulated in aqueous injection solutions which may contain antioxidants, buffers, bacteriostats, etc. Extemporaneous injection solutions may be prepared from sterile pills, granules, or tablets which may contain diluents, dispersing and surface active agents, binders and lubricants which materials are all well known to the ordinary skilled artisan.

In the case of oral administration, fine powders or granules of the compound may be formulated with diluents and dispersing and surface active agents, and may be prepared in water or in a syrup, in capsules or cachets in the dry state or in a non-aqueous suspension, where a suspending agent may be included. The compounds may also be administered in tablet form along with optional binders and lubricants, or in a suspension in water or syrup or an oil or in a water/oil emulsion and may include flavoring, preserving, suspending, thickening, and emulsifying agents. The granules or tablets for oral adminstration may be coated or other pharmaceutically acceptable agents and formulation may be utilized which are all known to those skilled in the pharmaceutical art.

Solid or liquid carriers can also be used. Solid carriers include starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Ointments and creams are prepared using various well known hydrophilic and hydrophobic bases. Topical reservoirs suitably are prepared using known polymeric materials such as various acrylic-based polymers selected to provide desired release characteristics. Suppositories are prepared from standard bases such as polyethylene glycol and cocoa butter.

The method of treatment according to this invention comprises administering internally or topically to a subject an effective amount of the active compound. Doses of active compounds in the inventive method and pharmaceutical compositions containing same are an efficacious, nontoxic quantity selected from the range of 0.01 to 500 mg/kg of active compound, preferably 0.1 to 50 mg/kg. Persons skilled in the art using routine clinical testing are able to determine optium doses for the particular ailment being treated. The desired dose is administered to a subject from 1 to 6 or more times daily, intravenously, orally, rectally, parenterally, topically, or by inhalation.

The efficacy of the inventive compounds of this invention as bradykinin receptor antagonists can be determined using the bradykinin binding and tissue assays described herein. The results of these assays demonstrate that the novel cyclic compounds are potent, selective bradykinin receptor antagonists.

The following examples are illustrative of preferred embodiments of methods of preparation and compounds of the invention and are not to be construed as limiting the invention thereto.

EXAMPLES

The synthesis of the peptides of this invention including derivation, activation, and coupling of protected amino acid residues, and their purification, and the analytical methods for determining identity and purity are included in the general body of knowledge of peptide chemistry, as described in Houben Weyl *Methoden der Organischen Chemie,* (1974), Vol. 16, parts I & II for solution-phase synthesis, and in *Solid Phase Peptide Synthesis,* (1984), by Stewart and Young for synthesis by the solid phase method of Merrifield.

Any chemist skilled in the art of peptide synthesis can synthesize the peptides of this invention by standard solution methods or by manual or automated solid phase methods.

EXAMPLE 1

Preparation of

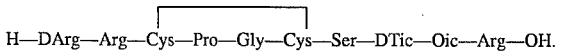

H—DArg—Arg—Cys—Pro—Gly—Cys—Ser—DTic—Oic—Arg—OH.

The peptide was synthesized employing FMOC chemistry on a solid phase synthesizer (Milligen Biosearch 9600 Peptide Synthesizer). FMOC-Arg(Pmc)-Wang resin (Bachem Bioscience) 1.00 g, with a resin substitution of 0.4 mmol Arg/gram of resin, was placed in the reaction vessel and subjected to procedure A for the coupling of FMOC-Oic. Commercially available amino acids were purchased from either Bachem Bioscience or Advanced Chemtech. Volumes of reagents and solvents were approximately 20 mL/gram of resin.

Procedure A

1. Deprotection: Removal of the flourene-methyleneoxycarbonyl protecting group (FMOC) was achieved by treatment of the resin with deblocking reageant (piperidine/toluene 1:1 v/v), two times for one minute and once for 20 minutes. The resin was then washed with (dichloromethane) DCM and dimethylformamide (DMF) several times.

2. Coupling: All couplings and recouplings were mediated in the same manner. FMOC-Oic (2.00 mmol in DMF) was mixed with 2.00 mmol di-isopropyl carbodiimide (DIPC) and 2.00 mmol hydroxybenzotriazole hydrate (HOBt) for two minutes prior to coupling with the resin. The mixture was added to the reaction vessel containing the resin and mixed for thirty minutes. Coupling efficiency of the amino acid to the growing peptide chain on the resin was checked. Incomplete coupling of an amino acid resulted in a recoupling step. Recoupling involved washing the resin-peptide three times for one minute with DCM and DMF. Amino acid activation with DIPC and HOBt with addition to the peptiode-resin was repeated and allowed to mix an additional thirty minutes. After a successful coupling the peptide resin was washed several times with DCM.

3. Capping: The growing peptide chain was capped on the a-amino group by acetylation with acetic anhydride (4 mmol) and triethylamine (4 mmol) in DMF at the end of each coupling or recoupling. The resin was washed three times with with DCM followed by three times with DMF. The resin was treated with capping reagent for ten minutes and then washed with DMF.

Procedure B

The N-terminal protecting group was removed by the following procedure:

Terminal deprotection: Following the successful coupling of the final amino acid to be added to the growing peptide chain, the peptide-resin was treated with deblocking reagent (piperidine/toluene) twice for one minute and once for twenty minutes. The resin was washed with DMF, DCM followed by methanol and dried by a stream of inerst gas (argon).

The following amino acids were added to the growing peptide chain according to the listed programs: FMOC-D-Tic, FMOC-Ser(t Bu), FMOC-Cys(t Bu), FMOC-Gly, FMOC-Pro, FMOC-Cys(t Bu), FMOC-Arg(Pmc), FMOC-D-Arg(Pmc). This yielded 1.6 g of dry peptide-resin.

TFA cleavage: The peptide-resin was treated with trifluoroacetic acid/methylene chloride/anisole (16 mL/16 mL/1.6 mL) and stirred at room temperature for one hour. The solvents were removed under reduced pressure using a rotary evaporator. The peptide resin was washed with di-ethyl ether, three times with 30 mL each time. The peptide was extracted into de-ionized water four times 25 mL and the solution was lyophilized to give crude peptide.

Purification of the linear peptide: The peptide was purified on a reverse phase C-18 (2×25 cm) Vydac HPLC column using a gradient of 0.1% TFAH$_2$O and acetonitrile (0.1% TFA) to give purified linear peptide.

Cyclization of the linear peptide: The purified linear peptide 0.05 mmol was dissolved in 350 mL methanol/water (1:6 v/v) and to this solution was added dropwise a solution of 13 mg iodine in 50 mL methanol with the aid of an addition funnel. After the addition of the iodine solution was complete the reaction vessel was placed in an ice bath and a solution of 1M sodium thiosulfate was added dropwise till the yellow color of the reaction mixture dissappeared. A slight excess of the sodium thiosulfate solution was added to the reaction vessel to ensure complete oxidation. The resulting solution was concentrated on a rotary evaporator and lyophilized to give crude cyclized peptide.

Purification of the cyclized peptide: The peptide was purified on a reverse phase C-18 (2×25 cm) Vydac HPLC column using a gradient of 0.1% TFAH$_2$O and acetonitrile (0.1% TFA) to give purified linear peptide.

Analysis: Purified peptide was chracterized by amino acid analysis and gave the following results: Arg, 2.92 (3.00); Ser, 0.96 (1.00); Gly 1.00 (1.00).

The peptide was also characterized by fast atom bombardment mass spectroscopy [M+H] obsd. 1243, [M+H] cald. 1243.

EXAMPLE 2

Preparation of

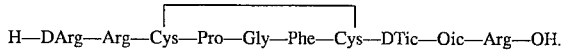

H—DArg—Arg—Cys—Pro—Gly—Phe—Cys—DTic—Oic—Arg—OH.

The peptide was synthesized employing FMOC chemistry on a solid phase synthesizer (Milligen Biosearch 9600 Peptide Synthesizer). FMOC-Arg(Pmc)-Wang resin (Bachem Bioscience) 1.00 g, with a resin substitution of 0.4 mmol Arg/gram of resin, was placed in the reaction vessel and subjected to procedure A for the coupling of FMOC-Oic. Commercially available amino acids were purchased from either Bachem Bioscience or Advanced Chemtech. Volumes of reagents and solvents were approximately 20 mL/gram of resin.

Procedure A

1. Deprotection: Removal of the flourene-methyleneoxycarbonyl protecting group (FMOC) was achieved by treatment of the resin with deblocking reageant (piperidine/toluene 1:1 v/v), two times for one minute and once for 20 minutes. The resin was then washed with (dichloromethane) DCM and dimethylformamide (DMF) several times.

2. Coupling: All couplings and recouplings were mediated in the same manner. FMOC-Oic (2.00 mmol in DMF) was mixed with 2.00 mmol di-isopropyl carbodiimide (DIPC) and 2.00 mmol hydroxybenzotriazole hydrate (HOBt) for two minutes prior to coupling with the resin. The mixture was added to the reaction vessel containing the rsin and mixed for thirty minutes. Coupling efficiency of the amino acid to the growing peptide chain on the resin was checked. Incomplete coupling of an amino acid resulted in a recoupling step. Reccoupling involved washing the resin-peptide three times for one minute with DCM and DMF. Amino acid activation with DIPC and HOBt with addition to the peptiode-resin was repeated and allowed to mix an additional thirty minutes. After a successful coupling the peptide resin was washed several times with DCM.

3. Capping: The growing peptide chain was capped on the a-amino group by acetylation with acetic anhydride (4 mmol) and triethylamine (4 mmol) in DMF at the end of each coupling or recoupling. The resin was washed three times with with DCM followed by three times with DMF.

The resin was treated with capping reagent for ten minutes and then washed with DMF.

Procedure B

The N-terminal protecting group was removed by the following procedure:

Terminal deprotection: Following the successful coupling of the final amino acid to be added to the growing peptide chain, the peptide-resin was treated with deblocking reagent (piperidine/toluene) twice for one minute and once for twenty minutes. The resin was washed with DMF, DCM followed by methanol and dried by a stream of inerst gas (argon).

The following amino acids were added to the growing peptide chain according to the listed programs: FMOC-DTic, FMOC-Cys(t Bu), FMOC-Phe, FMOC-Gly, FMOC-Pro, FMOC-Cys(t Bu), FMOC-Arg(Pmc), FMOC-D-Arg(Pmc). This yielded 1.5 g of dry peptide-resin.

TFA cleavage: The peptide-resin was treated with trifluoroacetic acid/methylene chloride./anisole (15 mL/15 mL/1.5 mL) and stirred at room temperature for one hour. The solvents were removed under reduced pressure using a rotary evaporator. The peptide resin was washed with di-ethyl ether, three times with 30 mL each time. The peptide was extracted into de-ionized water four times 25 mL and the solution was lyophilized to give crude peptide.

Purification of the linear peptide: The peptide was purified on a reverse phase C-18 (2×25 cm) Vydac HPLC column using a gradient of 0.1% TFAH$_2$O and acetonitrile (0.1% TFA) to give purified linear peptide.

Cyclization of the linear peptide: The purified linear peptide 0.05 mmol was dissolved in 350 mL methanol/water (1:6 v/v) and to this solution was added dropwise a solution of 13 mg iodine in 50 mL methanol with the aid of an addition funnel. After the addition of the iodine solution was complete the reaction vessel was placed in an ice bath and a solution of 1M sodium thiosulfate was added dropwise till the yellow color of the reaction mixture dissappeared. A slight excess of the sodium thiosulfate solution was added to the reaction vessel to ensure complete oxidation. The resulting solution was concentrated on a rotary evaporator and lyophilized to give crude cyclized peptide.

Purification of the cyclized peptide: The peptide was purified on a reverse phase C-18 (2×25 cm) Vydac HPLC column using a gradient of 0.1% TFAH$_2$O and acetonitrile (0.1% TFA) to give purified linear peptide.

Analysis: Purified peptide was chracterized by amino acid analysis and gave the following results: Arg, 2.9 (3.00); Phe, 0.9 (1.00); Gly 1.00 (1.00)

The peptide was also characterized by fast atom bombardment mass spectroscopy [M+H] obsd. 1303, [M+H] cald. 1303.

EXAMPLE 3

Preparation of

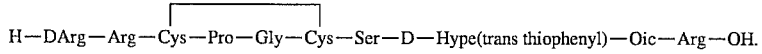
H—DArg—Arg—Cys—Pro—Gly—Cys—Ser—D—Hype(trans thiophenyl)—Oic—Arg—OH.

First, N-Boc-D-Hype (trans thiophenyl) was prepared according to Scheme II as follows:

To a stirred suspension of hexane washed sodium hydride (3.06 g, 80%, 38.1 mmol) in anhydrous tetrahydrofuran (95 mL) was added dropwise thiophenol (4.50 mL, 43.7 mmol) at room temperature (22° C.) under argon. After 1 hour, the mixture was treated with N-Boc-D-cis-4-(p-toluenesulfonyloxy)proline (5.00 g, 12.5 mmol) at room temperature. The resultant mixture was heated under reflux for 8 hours. After cooling to room temperature, the mixture was acidified to the Congo red indicator endpoint with aqueous hydrochloric acid. The solution was extracted with ethyl acetate (4×80 mL) and the combined extracts were dried over sodium sulfate. Concentration gave an oil which was used directly in the next step without purification.

To a stirred solution of the crude N-Boc-D-trans-4-phenylthioproline methyl ester in methol (20 mL) at room temperature was added a solution of sodium hydroxide (18 mL,3N). After two days at room temperature, water (30 mL) was added and the mixture was extracted with diethyl ether (3×45 mL). The combined organics were discarded and the aqueous layer was acidified with aqueous hydrochloric acid (5N) to the Congo red indicator endpoint. The aqueous layer was extracted with ethyl acetate (3×110 mL) and the the combined extracts were dried over sodium sulfate. Concentration followed by flash chromatography (silica gel, methylene chloride/methanol/acetic acid 90:8:2) gave N-Boc-D-Hype (trans thiophenyl) (3.64 g, 79.3%) as an oil: IR (neat film) cm$^1$ 3300–2500, 1749, 1702, 1583 (w), 1415, 1398, 1368, 1164, 743; $^1$H NMR (300 MHz, CDCl$_3$) ppm 1.45 & 1.48 (2×s, 9H), 2.31 (m, 1H), 3.44 (m, 1H), 3.76 (m, 2H), 4.43 (m, 1H), 7.37 (m, 3H), 7.42 (m, 2H), 9.77 (s, 1H).

Boc (D)-Hydroxy proline (4-trans thiophenyl) ether, 5.31 g (16.39 mmol) was treated with 8 mL trifluoroacetic acid in 8 mL methylene chloride for two hours at room temperature. The reaction mixture was evacuated using a rotary evaporator and the residue was dissolved in 20 mL dioxane and 70 mL 10% sodium carbonate solution, in an ice bath. pH of the resulting solution was 9 as checked by pH paper. To this solution was added a solution of 4.71 g (18.20 mmol) 9-fluorenylmethylene-oxycarbonyl chloride in 40 mL dioxane dropwise over a ten minute period. The reaction mixture was stirred overnight and poured into 100 mL water and washed with di-ethyl ether (3×100 mL), acidified to pH 2 with conc. hydrochloric acid and extracted with ethyl acetate (3×75 mL. The organic layer was washed with 0.1 N hydrochloric acid (3×50 mL) and saturated sodium chloride solution (3×50 mL), dried over magnesium sulfate and concentrated. The residue was crystallized using ether:hexane (1:1) and re-crystallized from boiling ether:hexane (1:1). Thin layer chromatography on silica gel using chloroform:methanol:acetic acid 90:8:2, showed one spot that was UV positive $r_f$ 0.68. NMR spectrum in $CDCl_3:DMSO$ $(d_6)$ 1:1 (60 mg/1.5 mL):
2.1–2.2 ppm (multiplet) (2H)
2.3–2.5 ppm (multiplet) (2H)
3.4 ppm (multiplet) (1H)
3.9 ppm (multiplet) (1H)
4.1–4.3 (multiplet) (2H)
4.4 ppm (multiplet) (doublet of doublet) (1H)
7.1–7.4 ppm (multiplet) (8H)
7.5 ppm (triplet) (1H)
7.6 ppm (doublet) (2H)
7.7 ppm (triplet) (2H)
Fast Atom Bombardment mass spectra showed [M+Na] 468.2 $[M]_{cald}$ 446.

The peptide was synthesized employing FMOC chemistry on a solid phase synthesizer (Milligen Biosearch 9600 Peptide Synthesizer). FMOC-Arg(Pmc)-Wang resin (Bachem Bioscience) 1.00 g, with a resin substitution of 0.4 mmol Arg/gram of resin, was placed in the reaction vessel and subjected to procedure A for the coupling of FMOC-Oic. Commercially available amino acids were purchased from either Bachem Bioscience or Advanced Chemtech. Volumes of reagents and solvents were approximately 20 mL/gram of resin.

Procedure A

1. Deprotection: Removal of the flourene-methyleneoxycarbonyl protecting group (FMOC) was achieved by treatment of the resin with deblocking reageant (piperidine/toluene 1:1 v/v), two times for one minute and once for 20 minutes. The resin was then washed with (dichloromethane) DCM and dimethylformamide (DMF) several times.

2. Coupling: All couplings and recouplings were mediated in the same manner. FMOC-Oic (2.00 mmol in DMF) was mixed with 2.00 mmol di-isopropyl carbodiimide (DIPC) and 2.00 mmol hydroxybenzotriazole hydrate (HOBt) for two minutes prior to coupling with the resin. The mixture was added to the reaction vessel containing the resin and mixed for thirty minutes. Coupling efficiency of the amino acid to the growing peptide chain on the resin was checked. Incomplete coupling of an amino acid resulted in a recoupling step. Recoupling involved washing the resin-peptide three times for one minute with DCM and DMF. Amino acid activation with DIPC and HOBt with addition to the peptiode-resin was repeated and allowed to mix an additional thirty minutes. After a successful coupling the peptide resin was washed several times with DCM.

3. Capping: The growing peptide chain was capped on the a-amino group by acetylation with acetic anhydride (4 mmol) and triethylamine (4 mmol) in DMF at the end of each coupling or recoupling. The resin was washed three times with with DCM followed by three times with DMF. The resin was treated with capping reagent for ten minutes and then washed with DMF.

Procedure B

The N-terminal protecting group was removed by the following procedure:

Terminal deprotection: Following the successful coupling of the final amino acid to be added to the growing peptide chain, the peptide-resin was treated with deblocking reagent (piperidine/toluene) twice for one minute and once for twenty minutes. The resin was washed with DMF, DCM followed by methanol and dried by a stream of inerst gas (argon).

The following amino acids were added to the growing peptide chain according to the listed programs: FMOC-D-Hype (trans thiophenyl), FMOC-Ser(t Bu), FMOC-Cys(t Bu), FMOC-Gly, FMOC-Pro, FMOC-Cys(t Bu), FMOC-Arg(Pmc), FMOC-D-Arg(Pmc). This yielded 1.6 g of dry peptide-resin.

TFA cleavage: The peptide-resin was treated with trifluoroacetic acid/methylene chloride/anisole ( 16 mL/16 mL/1.6 mL) and stirred at room temperature for one hour. The solvents were removed under reduced pressure using a rotary evaporator. The peptide resin was washed with diethyl ether, three times with 30 mL each time. The peptide was extracted into de-ionized water four times 25 mL and the solution was lyophilized to give crude peptide.

Purification of the linear peptide: The peptide was purified on a reverse phase C-18 (2×25 cm) Vydac HPLC column using a gradient of 0.1% $TFAH_2O$ and acetonitrile (0.1% TFA) to give purified linear peptide.

Cyclization of the linear peptide: The purified linear peptide 0.05 mmol was dissolved in 350 mL methanol/water (1:6 v/v) and to this solution was added dropwise a solution of 13 mg iodine in 50 mL methanol with the aid of an addition funnel. After the addition of the iodine solution was complete the reaction vessel was placed in an ice bath and a solution of 1M sodium thiosulfate was added dropwise till the yellow color of the reaction mixture dissappeared. A slight excess of the sodium thiosulfate solution was added to the reaction vessel to ensure complete oxidation. The resulting solution was concentrated on a rotary evaporator and lyophilized to give crude cyclized peptide.

Purification of the cyclized peptide: The peptide was purified on a reverse phase C-18 (2×25 cm) Vydac HPLC column using a gradient of 0.1% $TFAH_2O$ and acetonitrile (0.1% TFA) to give purified linear peptide.

Analysis: Purified peptide was chracterized by amino acid analysis and gave the following results: Arg, 2.92 (3.00); Ser, 0.96 (1.00); Gly 1.00 (1.00).

The peptide was also characterized by fast atom bombardment mass spectroscopy [M+H] obsd. 1243, [M+H] cald. 1243.

EXAMPLE 4

Bradykinin Binding Procedures

Binding of $^3$H-Bradykinin was performed using the method of D. C. Manning, R. Vavrek, J. M. Stewart, and S. H. Snyder, *J. Pharmacol. Exp. Ther.*, (1986), 237, 504. The tissues used in the binding assay were terminal ileum from male Hartley guinea pigs (150–350 g). After dissection, tissues were placed in 20 vol of ice-cold buffer A (25 mM TES containing 0.2 g/L of 1,10-phenanthroline adjusted of pH 6.8 with ammonium hydroxide) and homogenized using a Ploytron Tissumizer at setting 6 for 15 sec. The homogenate was centrifuged at 50,000×g for 10 min, the supernatant discarded, and the pellet resuspended in ice-cold buffer A by homogenization with the Polytron. Each tissue was homogenized and centrifuged three times. The final pellet was resuspended in buffer A containing bovine serum albumin (1 g/L) and Bacitracin (0.14 g/L) to a final volume of 170 mL/g of the original tissue weight. The binding assay consisted of 1 mM in 12×75 mm polyproproylene tubes: 50 μL ³H-bradykinin (20,000 dpm, ₁₈0.3 nM in the final assay volume), 100 μL displacing drug in buffer A, and 750 μL tissue homogenate. Each tray contained tubes, to which no drug was added to measure maximum binding and tubes to which bradykinin (1 μM final concentration) had been added, to measure specific binding. Specific binding accounted for 96–98% total binding. Tubes were incubated for 90 min at ambient temperature. The assays were terminated by filtration over Whatman GF/B glass fiber filters that had been pretreated for 2 hours with polyethyleneimine (2 g/L) using a Brandel Tissue Harvester, followed by washing with 4×1 mL aliquots of ice-cold 50 mM Tris, pH 7.4. Filters were dissolved in Ready-Safe Fluor (Beckman) for at least 90 min before quantitation by liquid scintillation spectrometry. Kd values were determined using saturation binding and analysis by EBDA (G. A. MacPherson, *J. Pharmacol. Methods*, (1985), 213), followed by LIGAND (P. J. Munson, D. Rodbard, *Anal. Biochem.*, (1980), 220). Ki values were determined using competitive analysis followed by EBDA and LIGAND. The following test results were obtained.

contraction, it was assumed that the maximum effect had been obtained and the tissue was washed to remove bradykinin and allowed to recover for 15 minutes. Antagonism of badykinin responses in the presence of antagonist were determined by repeating the cumulative addition procedure for bradykinin after the tissue has been exposed to the antagonist for 5 minutes. Three or four different concentrations of antagonist are studied sequentially in the same preparations. Responses were expressed as a percentage of the maximum contraction elicited by bradykinin in the absence of antagonist. $pA_2$ values were calculated by Schild analysis. The following results were obtained.

| Test Compound | $K_i$(nM) |
|---|---|
| H—DArg—Arg—Cys—Pro—Gly—Cys—Ser—DTic—Oic—Arg—OH | 1.5 ± .1 |
| H—DArg—Arg—Cys—Pro—Gly—Phe—Cys—DTic—Oic—Arg—OH | 14.8 ± .34 |
| H—DArg—Arg—Cys—Pro—Gly—Cys—Ser—D-Hype (trans thiophenyl)—Oic—Arg—OH | 2.15 ± .84 |

EXAMPLE 4

Determination of Bradykinin Antagonist Activity

The protocol was designed to identify compounds that possess antagonist activity at bradykinin receptors on intestinal (ileal longitudinal) smooth muscle.

| Test Compound | $pA_2$ |
|---|---|
| H—DArg—Arg—Cys—Pro—Gly—Cys—Ser—DTic—Oic—Arg—OH | 6.6 ± .16 |
| H—DArg—Arg—Cys—Pro—Gly—Cys—Ser—D-Hype (trans thiophenyl)—Oic—Arg—OH | 7.9 ± .1 |

Guinea pig intestine was removed and placed in a Petri dish containing Tyrodes solution and cut into 3–4 cm segments. The longitudinal muscle was separated from the underlying circular muscle using a cotton applicator (Paton and Zar, *J. Physiol.*, (1968), 194:13. Muscle strips were connected to isometric force-displacement transducers (Grass or Gould) coupled to a physiograph and placed in tissue baths containing Tyrode's solution at 37° C. Each preparation was suspended under a resting tension of 2 g.

After equilibration of the tissues, appropriate volumes of bradykinin solutions were cumulatively added to the 10 mL tissue baths to increase the concentration of bradykinin in the bath step-by-step without washing out after each single dose. Higher concentrations were added only after the preceding contraction had reached a steady value. When the next concentration step does not cause a further increase in The invention being thus described, it will be obvious that the same may be varied in many ways. Such variations are not to be regarded as a departure from the spirit and scope of the invention and all such modifications are intended to be included within the scope of the following claims.

We claim:

1. A cyclic peptide which has an affinity for the bradykinin receptor having the formula:

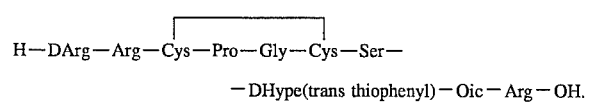

* * * * *